United States Patent
Bigner et al.

(10) Patent No.: US 9,249,217 B2
(45) Date of Patent: Feb. 2, 2016

(54) BISPECIFIC EGFRVIII X CD3 ANTIBODY ENGAGING MOLECULES

(75) Inventors: Darell D. Bigner, Mebane, NC (US); Chien-Tsun Kuan, Cary, NC (US); John H. Sampson, Durham, NC (US); Mingqing Cai, Danbury, CT (US); Bryan D. Choi, Durham, NC (US); Ira H. Pastan, Potomac, MD (US)

(73) Assignees: Secretary, DHHS, Rockville, MD (US); Duke University, Durham, NC (US)

( * ) Notice: Subject to any disclaimer, the term of this patent is extended or adjusted under 35 U.S.C. 154(b) by 0 days.

(21) Appl. No.: 13/296,809

(22) Filed: Nov. 15, 2011

(65) Prior Publication Data

US 2012/0189630 A1    Jul. 26, 2012

Related U.S. Application Data

(60) Provisional application No. 61/419,347, filed on Dec. 3, 2010.

(51) Int. Cl.
 *C12N 15/10* (2006.01)
 *C07K 16/28* (2006.01)
 *C07K 16/30* (2006.01)
 *A61K 39/00* (2006.01)

(52) U.S. Cl.
 CPC ......... *C07K 16/2809* (2013.01); *C07K 16/2863* (2013.01); *A61K 2039/505* (2013.01); *C07K 2317/31* (2013.01); *C07K 2317/622* (2013.01); *C07K 2317/73* (2013.01); *C07K 2317/92* (2013.01)

(58) Field of Classification Search
 None
 See application file for complete search history.

(56) References Cited

U.S. PATENT DOCUMENTS

| | | | |
|---|---|---|---|
| 5,585,097 A | | 12/1996 | Bolt et al. |
| 5,821,336 A | * | 10/1998 | Odink et al. |
| 5,929,212 A | | 7/1999 | Jolliffe et al. |
| 5,968,509 A | | 10/1999 | Gorman et al. |
| 6,723,538 B2 | | 4/2004 | Mack et al. |
| 7,129,332 B2 | | 10/2006 | Pastan et al. |
| 7,235,641 B2 | | 6/2007 | Kufer et al. |
| 7,728,114 B2 | | 6/2010 | Mach et al. |
| 7,736,644 B2 | * | 6/2010 | Weber et al. |
| 7,820,166 B2 | | 10/2010 | Lanzavecchia |
| 7,994,289 B2 | | 8/2011 | Waldmann et al. |
| 8,007,796 B2 | | 8/2011 | Baeuerle et al. |
| 8,076,459 B2 | | 12/2011 | Hofmeister et al. |
| 8,101,722 B2 | | 1/2012 | Kufer et al. |

(Continued)

FOREIGN PATENT DOCUMENTS

WO    WO 2008119567 A2 * 10/2008

OTHER PUBLICATIONS

Gajadhar et al., In situe analysis of mutant EGFRs prevalent in glioblastoma multiforme reveals aberrant dimerization, activation, and differential response to anti-EGFR targeted therapy, Mol. Canc. Res., 10:428-440, 2012.*

(Continued)

*Primary Examiner* — Claire Kaufman
(74) *Attorney, Agent, or Firm* — Banner & Witcoff, LTD.

(57) ABSTRACT

We have constructed bispecific antibody engaging molecules which have one arm that specifically engages a tumor cell which expresses the human EGFRvIII mutant protein on its surface, and a second arm that specifically engages T cell activation ligand CD3. The engaging molecules are highly cytotoxic and antigen-specific.

6 Claims, 8 Drawing Sheets

(56) References Cited

U.S. PATENT DOCUMENTS

2010/0150918 A1* 6/2010 Kufer et al.
2010/0183554 A1 7/2010 Mach et al.

OTHER PUBLICATIONS

Shalaby et al., Development of bispecific antibodies reactive with cytotoxic lymphocytes and tumor cells overexpressing the HER2 protooncogene, J. Exp. Med. 175:217-225, Jan. 1, 1992.*
Lutterbuese et al. Supplemental Information, Proceedings of the Natl. Acad. Sci, USA, Jul. 2010, 10.1073/pnas.1000976107 [online], [retrieved on Apr. 23, 2013] Retrieved from the Internet <URL: http://www.pnas.org/content/suppl/2010/06/25/1000976107. DCSupplemental/pnas.201000976SI.pdf.*
Gruber et al., Efficient tumor cell lysis mediated by a bispecific single chain antibody expressed in *Eschericia coli*, 152(11):5368-74, Jun. 1, 1994.*
Kipriyanov et al., Effect of domain order on the activity of bacterially produced bispecific single-chain Fv antibodies, J. Mol. Biol. 330(1):99-111, Jun. 27, 2003.*
Hayashi et al. A highly effective and stable bispecific diabody for cancer immunotherapy: cure of xenografted tumors by bispecific diabody and T-LAK cells, Cancer Immunol. Immunother. 53:497-509, 2004.*
Mack et al., Biologic properties of a bispecific single-chain antibody directed against 17-1A(EpCAM) and CD3, J. Immunol. 158:3965-3970, 1997.*
Bera et al., A bivalent disulfide-stabilized Fv with improved antigen binding to erbB2, J. Mol. Biol. 281:475-483,1998.*
Choi et al., 2013, Proc. Natl. Acad. Sciences USA, 110:270-275.
Bargou, Ralf, et al, "Tumor Regression in Cancer Patients by Very Low Doses of a T Cell-Engaging Antibody," Science, vol. 321, Aug. 15, 2008, pp. 974-977, downloaded from www.sciencemag.org.
Mack, Matthias, et al., "A small bispecific antibody construct expressed as a functional single-chain molecule with high tumor cell cytotoxicity," Proc. Natl. Acad. Sci USA, vol. 92, Jul. 1995, pp. 7021-7025.
Lutterbuese, Ralf, et al., "T cell-engaging BiTE antibodies specific for EGFR potently eliminate KRAS- and BRAF-mutated colorectal cancer cells," PNAS, vol. 107 No. 7, Jul. 30, 2010, pp. 12605-12610.
Cai M, Choi B, Bigner D, Sampson J, Kuan C. A bispecific T-cell engager effectively eradicates EGFRvIII-expressing glioblastoma multiforme [abstract]. In: Proceedings of the 101st Annual Meeting of the American Association for Cancer Research; Apr. 17-21, 2010; Washington, DC. Philadelphia (PA): AACR; 2010. Abstract nr 4409.
C. T. Kuan, M. Cai, B. Choi, J. H. Sampson, D. D. Bigner (Durham, USA). A bispecific T cell-engaging antibody effectively eradicates EGFRvIII-expressing glioblastoma multiforme. The 18th International Conference on Brain Tumor Research and Therapy; May 18-20, 2010; Travemunde, Germany.
Chien-Tsun Kaun et al., "Increased Binding Affinity Enhances Targeting of Glioma Xenografts by EGFRvIII-Specific scFV," Int. J. Cancer: 88, 962-969 (2000), Publication of the International Union Against Cancer.
Choi BD, Gedeon PC, Kuan CT, Sanchez-Perez L, Archer GE, Bigner DD, et al. Rational design and generation of recombinant control reagents for bispecific antibodies through CDR mutagenesis. Journal of immunological Methods. Jun. 24, 2013. pii: S0022-1759(13)00175-0. doi: 10.1016/j.jim.2013.06.003.

* cited by examiner

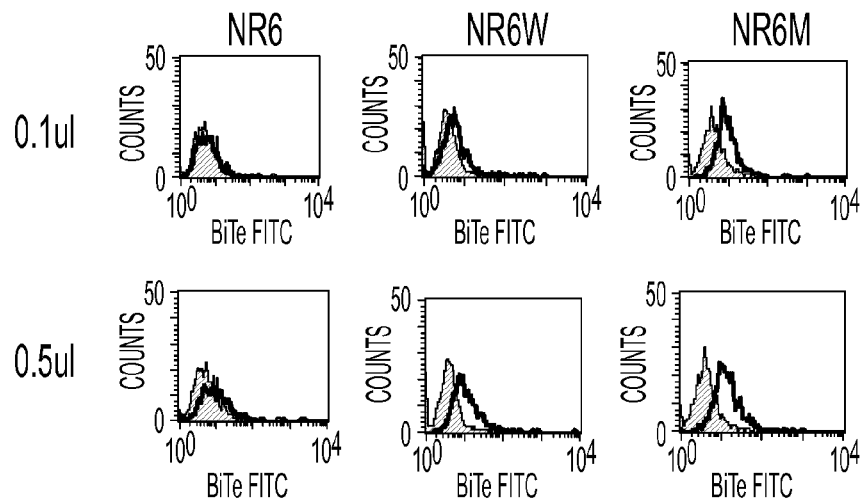
FIG. 6A
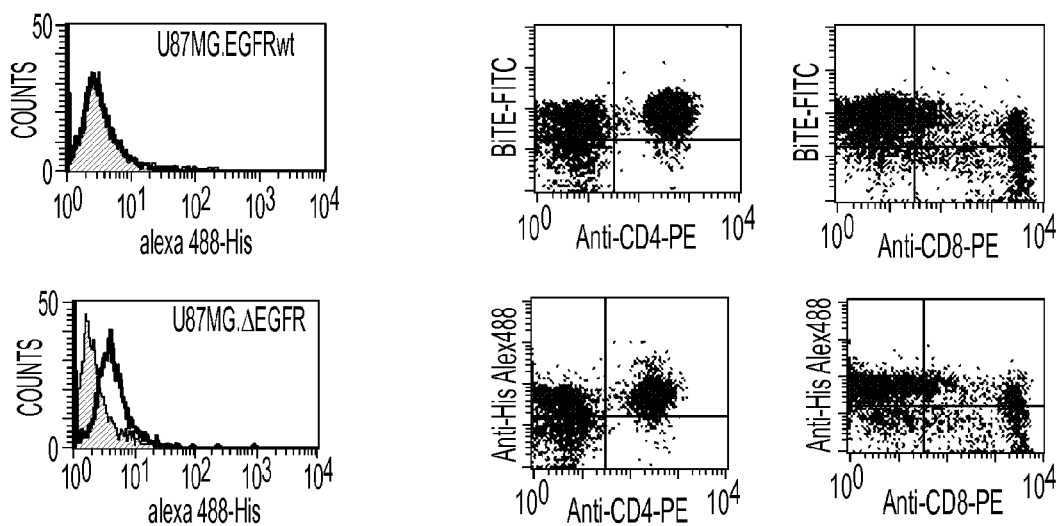
FIG. 6B
FIG. 7

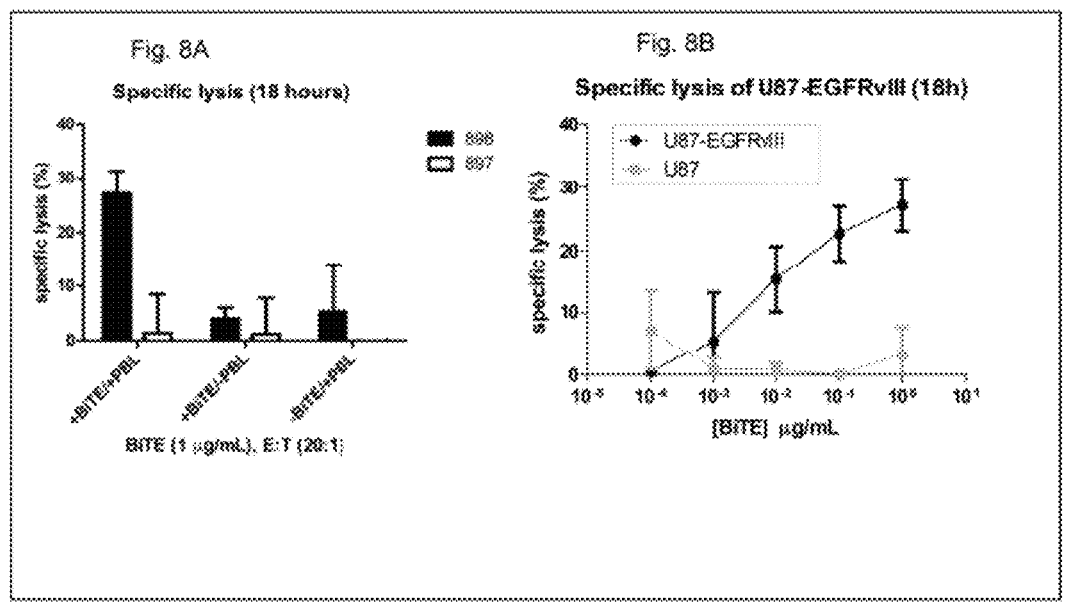
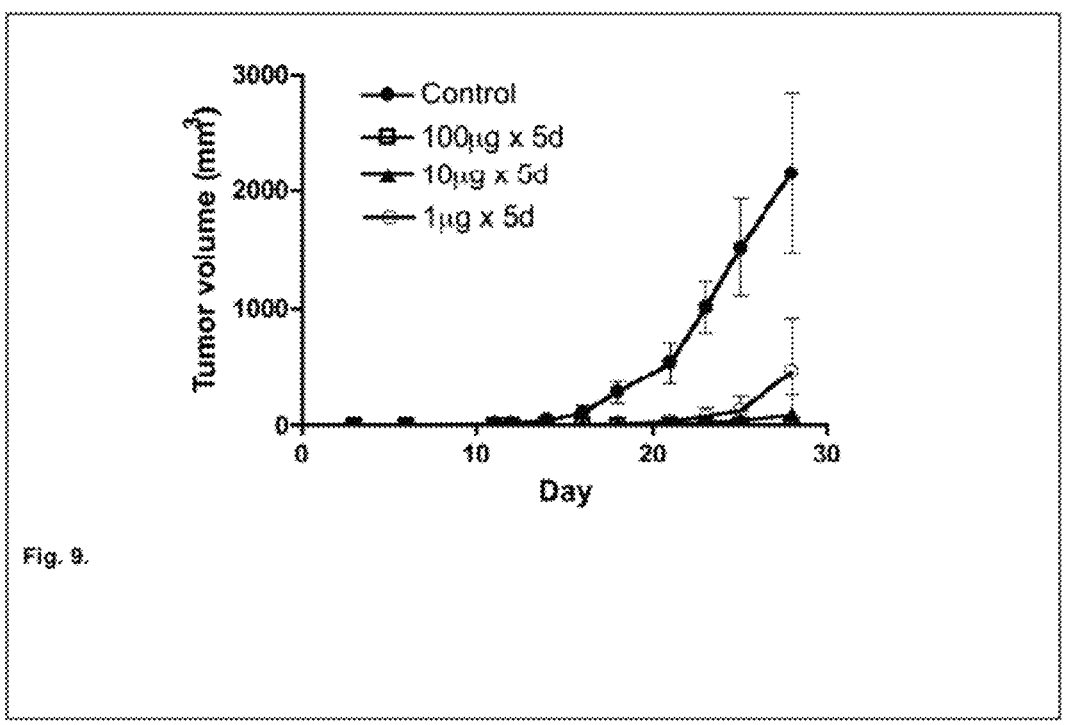
Fig. 9.

BISPECIFIC EGFRVIII X CD3 ANTIBODY ENGAGING MOLECULES

This invention was made using funds from the U.S. government. The U.S. government retains certain rights in the invention according to the terms of NIH/NCI grant no. CA11898.

TECHNICAL FIELD OF THE INVENTION

This invention is related to the area of cancer therapy. In particular, it relates to treating cancers that express EGFRvIII.

BACKGROUND OF THE INVENTION

The most common primary malignant brain tumor, glioblastoma multiforme (GBM), remains uniformly fatal despite surgical resection, radiation therapy, and chemotherapy1. Immunotherapy promises to induce robust, tumor-specific immune responses that eliminate neoplastic cells with unparalleled specificity without adding additional toxicity to multimodality therapy. Substantial evidence supports the role of T-cells in the eradication of cancer. Recently, the concept of using specific antibodies to re-direct T-cells has been optimized in the form of recombinant bispecific T-cell engaging molecules, or bispecific T-cell engaging molecules, that consist of a tumor-targeting single-chain antibody connected to a single-chain antibody directed against a Tcell activation ligand such as CD3. These bispecific T cell engaging molecules can tether T-cells to tumor cells, which results in a highly localized and specific activation of T-cells with concomitant tumor cell lysis. Recently, human trials using a CD19×CD3 bispecific T cell engaging molecule confirmed the potency of these constructs by tumor regression observed in 7/7 patients with non-Hodgkin's lymphoma at a dose of only 0.06 mg/m2 with clearance of tumor from the blood, bone marrow, and liver4. The most significant limitation of these promising constructs, however, is the lack of tumor-specific targets that are frequently and homogeneously expressed.

Tumor-specific antigens derived from mutations in somatic genes are less likely to be associated with autoimmunity, but often arise randomly as a result of the genetic instability of tumors and, as such, tend to be patient-specific and incidental to the oncogenic process. EGFRvIII, however, is a frequent and consistent tumor specific mutation, central to the neoplastic process, which consists of an in-frame deletion of 801 base pairs from the extracellular domain (ECD) of the EGFR that splits a codon and produces a novel glycine at the fusion junction. This mutation encodes a constitutively active tyrosine kinase that enhances neoplastic cell growth and migration9 and confers radiation and chemotherapeutic resistance to tumor cells. The EGFRvIII mutation is most frequently seen in patients with GBM, but has been found in a broad array of other common cancers. The new glycine inserted at the fusion junction of normally distant parts of the ECD results in a tumor-specific epitope (FIG. 1) that is not found in any normal tissues.

There is a continuing need in the art to find better and more successful treatments of cancers such as brain cancers.

SUMMARY OF THE INVENTION

One aspect of the invention is a bispecific polypeptide. The bispecific polypeptide comprises a first single chain variable region which binds to EGFRvIII. The first single chain variable region is in series with a second single chain variable region. The second single chain variable region binds to a T cell activation ligand, such as CD3.

Another aspect of the invention is a polynucleotide encoding a bispecific polypeptide. The bispecific polypeptide comprises a first single chain variable region which binds to EGFRvIII. The first single chain variable region is in series with a second single chain variable region. The second single chain variable region binds to a T cell activation ligand, such as CD3.

Another aspect of the invention is a method of treating an EGFRvIII-expressing tumor. A bispecific polypeptide is administered to the patient, whereby a cytolytic T cell response to the tumor is induced. The bispecific polypeptide comprises a first single chain variable region which binds to EGFRvIII. The first single chain variable region is in series with a second single chain variable region. The second single chain variable region binds to a T cell activation ligand, such as CD3.

Still another aspect of the invention is a method of making a bispecific polypeptide. A cell is cultured in a culture medium. The cell comprises a polynucleotide encoding a bispecific polypeptide. The bispecific polypeptide comprises a first single chain variable region which binds to EGFRvIII. The first single chain variable region is in series with a second single chain variable region. The second single chain variable region binds to a T cell activation ligand, such as CD3. After culturing, the bispecific polypeptide is harvested from the cells or from the culture medium.

These and other embodiments which will be apparent to those of skill in the art upon reading the specification provide the art with

BRIEF DESCRIPTION OF THE DRAWINGS

FIG. 3A: Serum titers of GBM patients were tested by ELISA against EGFRvIII-specific PEPvIII after each vaccination. FIG. 3B: Binding of a patient serum sample to EGFRvIII ECD assayed by BIAcore analysis.

FIG. 4A(Left): Fluorescent cytometry analysis of supernatant derived from human B-cells of a vaccinated GBM patient (ACT II-18) that were stimulated with PEPvIII on EGFRvIII-transfected 3T3 fibroblasts (NR6M) and wild-type EGFR transfectants (NR6W). FIG. 4B (Middle): Two weeks after stimulation, supernatants are analyzed for specificity using NR6M cells or NR6W cells. Supernatant from transformed human B-cells can produce antibodies recognizing NR6M cells. FIG. 4C (Right): E4, G5 and F12 were single-well picked from a 96-well plate of the patient sample Act II-18 after B cells were enriched with a human B cell enrichment kit (Stem Cell #19054). Patient peripheral blood mononuclear cells are transformed with 20% EBV virus (95.8 cell supernatant) in the presence of 10 mg/mL of cyclosporine. To improve the transformation efficiency, CpG 2006 was added at 2.5 ng/mL.

FIG. 6A-6B shows the binding of MR1-1×CD3 bispecific T cell engaging molecule. FIG. 6A(Left): Binding to NR6M and NR6W cells. As expected, MR1-1 shows some binding to wild-type EGFR at higher concentrations. FIG. 6B (Right): Binding of MR1-1-bispecific T cell engaging molecule to human GBM cell lines. U87MG.EGFR (wild type) (top) and U87MG.ΔEGFRvIII (bottom) stained with MR1-1×CD3 bispecific T cell engaging molecule.

FIG. 7 shows the binding of MR1-1×CD3 bispecific T cell engaging molecule to CD3-expressing human PBMC by flow cytometry. In the top panels, MR1-1 bispecific T cell engaging molecule was labeled with FITC and stained the PBMC cells directly together with anti-CD4 or anti-CD8-PE. In the bottom panels, binding of MR1-1 bispecific T cell engaging molecule to cells was detected by anti-His Alex 488.

FIG. 8A-8B shows MR1-1×CD3 mediates dose-dependent specific lysis in vitro. Redirected lysis of glioma cell line U87MG (897) and U87MG-EGFRvIII (898) was tested with human PBL in the presence of increasing bispecific T cell engaging molecule concentrations for an 18-h assay period. Effector and target cells were mixed at an E:T ratio of 20:1. Error bars indicate SD of triplicate measurements. Specific lysis was assessed via standard chromium release assay.

FIG. 9 shows dose-dependent inhibition of subcutaneous U87MG-EGFRvIII tumor growth in NSG mice by MR1-1× CD3. $3\times10^5$ U87MG-EGFRvIII cells were mixed with $3\times10^5$ human PBLs (E:T of 1:1) and subcutaneously injected into the right flanks of 8 male NSG mice per group. Treatment by tail vein injections with 1 μg, 10 μg, 100 μg, and vehicle control was started 1 h after implantation of tumor cells. Treatment was repeated for four consecutive days. Tumors were measured three times a week with calipers.

Figure 10:
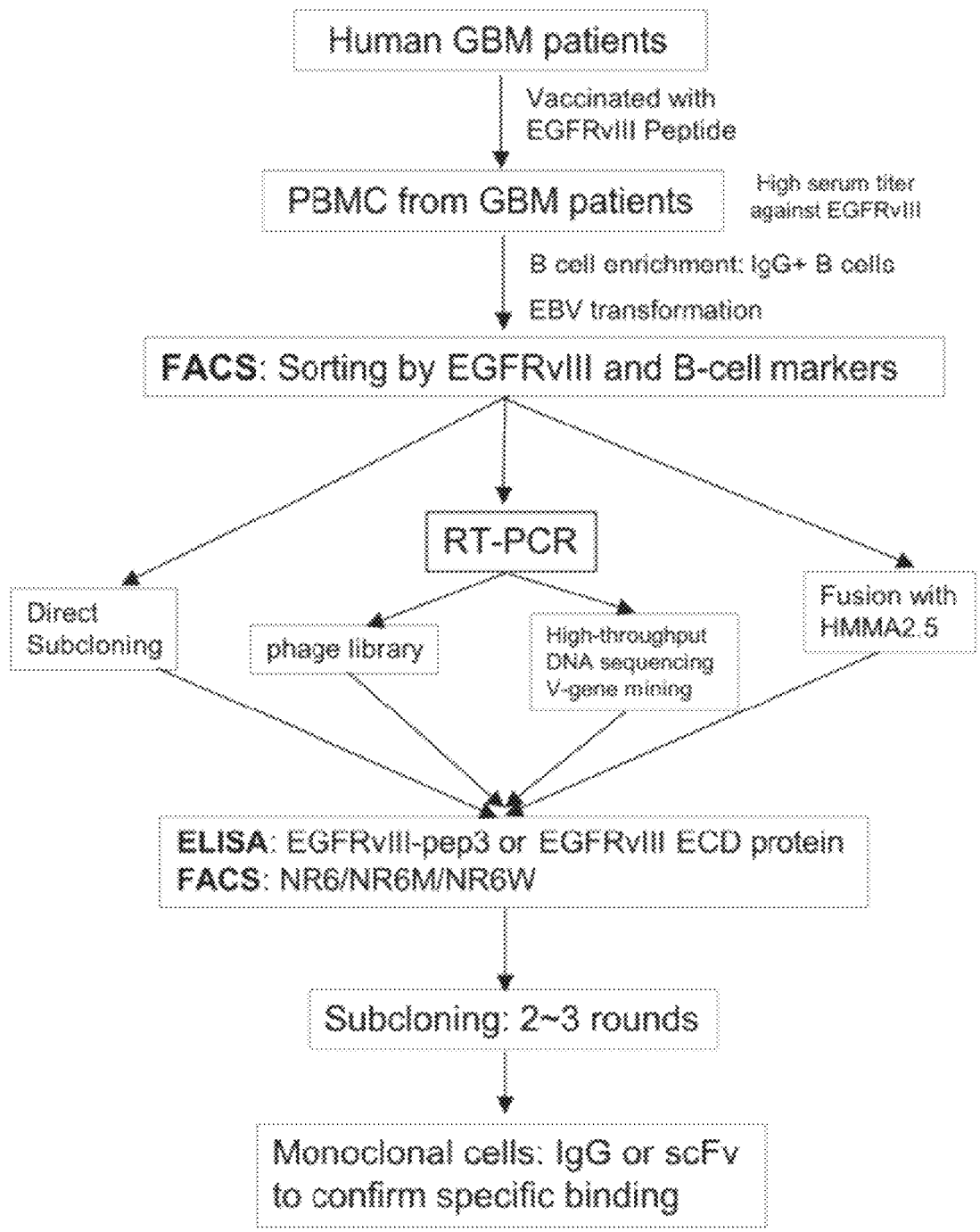

FIG. 10 is a flow diagram detailing the cloning of a fully human anti-EGFRvIII antibody from GBM patients.

DETAILED DESCRIPTION OF THE INVENTION

The inventors have developed specific bispecific T cell engaging molecules which target both the EGFRvIII and a T cell activation ligand, such as CD3. They have been found to recruit cytotoxic T cells to a cancer cell expressing EGFRvIII and activate cytotoxic T cells, thereby killing the cancer cell expressing the EGFRvIII molecule. The bispecific T cell engaging molecules are selectively reactive with EGFRvIII and a T cell activation ligand, such as CD3 displayed on the surface of mammalian cells which are accessible to the antibody from the extracellular milieu.

The species of mammal from which the constituent antibody portions of the bispecific T cell engaging molecules are derived can be many. Mouse, sheep, goat, rat, human, macaque, baboon, may be used as is convenient. The separate portions of the bispecific T cell engaging molecules may come from the same or different species. For example, a mouse/human, or a human/mouse bispecific T cell engaging molecule can be made. But, human/human may be the most advantageous clinically, for reduced induction of neutralizing antibodies. Mouse/mouse may be most useful in preclinical studies using, for example xenograft models in immunodeficient mice.

Many types of bispecific antibodies can be constructed and used. These include, without limitation, quadroma-derived F(ab')2, heterodimeric scFv, heterodimeric Fab, diabodies, tandem diabodies, and tandem scFv molecules. Bispecific antibodies can also be made using trifunctional antibodies, i.e., antibodies that have a third specificity as well as the initial two for EGFRvIII and a T cell activation ligand. The many forms are well known in the art.

Once bispecific T cell engaging molecules have been constructed, they can be produced in recombinant cells. Any suitable cell type can be used. If the bispecific T cell engaging molecules are secreted, they can be harvested from the culture medium. If they remain intracellular, the cells can be collected and broken under suitable conditions to harvest the bispecific T cell engaging molecules from the appropriate cell fraction. Any convenient cell host can be used for producing the bispecific T cell engaging molecules, including bacteria, yeast, insect cells, plant cells, algal cells, mammalian cells. In one scenario, the bispecific T cell engaging molecules can be produced in stably transfected CHO cells and the supernatant will contain the produced bispecific T cell engaging molecules.

Any tumor which expresses EGFRvIII can be targeted and treated with the bispecific T cell engaging molecules. Tumors which have been found to express the EGFRvIII antigen include brain tumors such as glioblastoma multiforme, breast tumors, and lung tumors. Any of these or other tumors can be targeted if it expresses the mutant antigen.

DEFINITIONS

Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the disclosure which can be had by reference to the specification as a whole. Accordingly, the terms defined immediately below are more fully defined by reference to the specification in its entirety.

"EGFRvIII" means a mutant form of the epidermal growth factor receptor recognized by MR1 scFv and characterized by an 801 base pair in frame deletion of exons 2 to 7 near the amino terminal. This form of the receptor is known in the art, as exemplified by the Wickstrand et al., Moscatello et al., and Lorimer et al. references cited in the Background. Due to a change in terminology, EGFRvIII was originally termed a Type II mutation in some earlier work in the field, as exemplified by U.S. Pat. No. 5,212,290.

The term "CD3" refers to the protein complex associated with the T cell receptor. Antibodies directed against CD3 are able to generate an activation signal in T lymphocytes. Other T cell activation ligands can be used as well, including without limitation CD28, CD134, CD137, and CD27.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments (See, U.S. Ser. No. 08/077,252, incorporated herein by reference), or pFv fragments (See, U.S. Provisional Patent Applications 60/042,350 and 60/048,848, both of which are incorporated herein by reference.). The term "antibody" also includes antigen binding forms of antibodies (e.g., Fab', F(ab')2, Fab, Fv and rIgG (See also, Pierce Catalog and Handbook, 1994-1995 (Pierce Chemical Co., Rockford, Ill.).

An antibody immunologically reactive with a particular antigen can be generated by recombinant methods such as selection of libraries of recombinant antibodies in phage or similar vectors (See, e.g., Huse, et al., Science 246:1275-1281 (1989); Ward, et al., Nature 341:544-546 (1989); and Vaughan, et al., Nature Biotech. 14:309-314 (1996)).

Typically, an immunoglobulin has a heavy and light chain. Each heavy and light chain contains a constant region and a variable region. Light and heavy chain variable regions contain a "framework" region interrupted by three hypervariable regions, also called complementarity-determining regions or CDRs. The extent of the framework region and CDRs have been defined (see, SEQUENCES OF PROTEINS OF IMMUNOLOGICAL INTEREST, Kabat, E., et al., U.S. Department of Health and Human Services, (1987); which is incorporated herein by reference). The sequences of the framework regions of different light or heavy chains are relatively conserved within a species. The framework region of an antibody, that is the combined framework regions of the constituent light and heavy chains, serves to position and align the CDRs in three dimensional space. The CDRs are primarily responsible for binding to an epitope of an antigen. The CDRs are typically referred to as CDR1, CDR2, and CDR3, numbered sequentially starting from the N-terminus.

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable heavy chain to the variable light chain. The linker may be a series of a single amino acid or an alternating pattern of amino acids, for example.

The term "contacting" includes reference to placement in direct physical association. With regards to this invention, the term refers to antibody-antigen binding.

As used herein, the term "bispecific T-cell engaging molecule" refers to a molecule designed to harness a subject's T cells to kill cancer cells by targeting to the tumor cells expressing a desired molecule. In certain embodiments, the desired molecule is human EGFRvIII. In other embodiments, the bispecific T cell engaging molecules comprises two Fv domains. In other embodiments, the bispecific T cell engaging molecule comprises a first Fv domain directed to EGFRvIII and a second Fv domain directed to CD3. The Fv domains may be scFv domains.

The term "selectively reactive" includes reference to the preferential association of an antibody, in whole or part, with a cell or tissue bearing EGFRvIII or CD3 and not to cells or tissues lacking EGFRvIII or CD3. It is, of course, recognized that a certain degree of non-specific interaction may occur between a molecule and a non-target cell or tissue. Nevertheless, selective reactivity, may be distinguished as mediated through specific recognition of EGFRvIII and CD3. Although selectively reactive antibodies bind antigen, they may do so with low affinity. On the other hand, specific binding results in a much stronger association between the antibody and cells bearing EGFRvIII or CD3 than between the bound antibody and cells lacking EGFRvIII or CD3 or low affinity antibody-antigen binding. Specific binding typically results in greater than 2-fold, preferably greater than 5-fold, more preferably greater than 10-fold and most preferably greater than 100-fold increase in amount of bound antibody (per unit time) to a cell or tissue bearing EGFRvIII or CD3 as compared to a cell or tissue lacking EGFRvIII or CD3. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity. In some embodiments of the invention the antibody will bind to EGFRvIII better than to wild-type EGFR. In some instances an antibody will bind to both. The differential binding may be reflected in a stronger binding, or in a faster binding, or in more binding to a fixed amount of antigen with a fixed amount of time. The better binding may be by a factor of at least 2, 4, 6, 8, or 10. Under some disease conditions, it may be advantageous to have some degree of binding to both mutant and wild-type forms of EGFR, for example where both forms are co-expressed on a tumor target. Under other disease situations, it may be desirable to have the maximum amount of specify available for the mutant form, for example, to reduce adverse side effects.

As used herein, "polypeptide," "peptide," and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody. Cysteine residues can be introduced, e.g., by site directed mutagenesis, so that stabilizing disulfide bonds can be made within the molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under expressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium Mycoplasma capricolum (Proc. Nat'l Acad. Sci. USA 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as E. coli, or eukaryotic cells such as yeast, insect, amphibian, or mammalian cells.

The phrase "phage display library" refers to a population of bacteriophage, each of which contains a foreign cDNA recombinantly fused in frame to a surface protein. The phage displays the foreign protein encoded by the cDNA on its surface. After replication in a bacterial host, typically E. coli, the phage which contain the foreign cDNA of interest are selected by the expression of the foreign protein on the phage surface.

"Sequence identity" in the context of two nucleic acid or polypeptide sequences includes reference to the nucleotides (or residues) in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers & Miller, Computer Applic. Biol. Sci. 4:11-17 (1988), e.g., as implemented in the program PC/GENE (Intelligenetics, Mountain View, Calif., USA). An indication that two peptide sequences are substantially similar is that one peptide is immunologically reactive with antibodies raised against the second peptide. Thus, a peptide is substantially similar to a second peptide, for example, where the two peptides differ only by a conservative substitution.

A "comparison window", as used herein, includes reference to a segment of about 10-20 residues in which a sequence may be compared to a reference sequence of the same number of contiguous positions after the two sequences are optimally aligned. Methods of alignment of sequences for comparison are well known in the art. Optimal alignment of sequences for comparison may be conducted by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l Acad. Sci. USA 85:2444 (1988); by computerized implementations of these algorithms (including, but not limited to CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), Madison, Wis., USA); the CLUSTAL program is well described by Higgins & Sharp, Gene 73:237-244 (1988) and Higgins & Sharp, CABIOS 5:151-153 (1989); Corpet, et al., Nucl. Acids Res. 16:10881-90 (1988); Huang, et al., Computer Applications in the Biosciences 8:155-65 (1992); and Pearson, et al., Meth. in Molec. Biol. 24:307-31 (1994).

The terms "effective amount" or "amount effective to" or "therapeutically effective amount" include reference to a dosage of a therapeutic agent sufficient to produce a desired result, such as inhibiting cell protein synthesis by at least 50%, or killing the cell.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient.

The term "in vivo" includes reference to inside the body of the organism from which the cell was obtained. "Ex vivo" and "in vitro" means outside the body of the organism from which the cell was obtained.

Once the nucleic acids encoding a bispecific T cell engaging molecule of the present disclosure are isolated and cloned, one may express the desired protein in a recombinantly engineered cell such as bacteria, plant, yeast, insect, and mammalian cells. It is expected that those of skill in the art are knowledgeable in the numerous expression systems available for expression of proteins including E. coli, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes. It is also contemplated that the DNA can be delivered to a recipient patient, for example, on nanoparticles or other DNA delivery system, and that the patient may produce her own bispecific T-cell engaging molecules in vivo.

One of skill would recognize that modifications can be made to a nucleic acid encoding a polypeptide of the present disclosure (i.e., anti-EGFRvIII or anti-CD3) without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

The phrase "malignant cell" or "malignancy" refers to tumors or tumor cells that are invasive and/or able to undergo metastasis, i.e., a cancerous cell.

In addition to recombinant methods, the bispecific T cell engaging molecules of the present disclosure can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. J. Am. Chem. Soc. 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

In addition to redirecting T-cells to tumor-specific antigens, the bispecific T cell engaging molecules can also be used to carry other diagnostic or therapeutic compounds to cells expressing EGFRvIII on their surface. Thus, a bispecific T cell engaging molecule may be attached directly or indirectly, e.g., via a linker, to a drug so that it will be delivered directly to cells bearing EGFRvIII. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to the bispecific T cell engaging molecule may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., Pharm. Ther. 28:341-365 (1985).

The bispecific T cell engaging molecules of this disclosure are particularly useful for parenteral administration, such as intravenous administration or administration into a body cavity or lumen of an organ. For example, ovarian malignancies may be treated by intravenous administration or by localized delivery to the tissue surrounding the tumor. For treatment of tumors in the brain, the molecules may be delivered directly to the brain, for example by injection or the molecules can be administered intravenously and then cross the blood brain barrier.

The compositions for administration will commonly comprise a solution of the bispecific T cell engaging molecules dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the pharmaceutical compositions of the present disclosure can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339 (1992) both of which are incorporated herein by reference.

Polymers can be used for ion-controlled release of pharmaceutical compositions of the present invention. Various degradable and nondegradable polymeric matrices for use in controlled drug delivery are known in the art (Langer, R., Accounts Chem. Res. 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425-434 (1992); and Pec, et al., J. Parent. Sci. Tech. 44(2):58-65 (1990)). Alternatively, hydroxyapatite has been used as a microcarrier for controlled release of proteins (Ijntema, et al., Int. J. Pharm. 112:215-224 (1994)). In yet another aspect, liposomes are used for controlled release as well as drug targeting of the lipid-capsulated drug (Betageri, et at., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235, 871, 4,501,728, 4,837,028 4,957,735 and 5,019,369, 5,055, 303; 5,514,670; 5,413,797; 5,268,164; 5,004,697; 4,902,505; 5,506,206, 5,271,961; 5,254,342 and 5,534,496, each of which is incorporated herein by reference.

Among various uses of the bispecific T cell engaging molecules of the present invention are included a variety of disease conditions caused by specific human cells that may be eliminated by the toxic action of the fusion protein. One preferred application for the bispecific T cell engaging molecules of the invention is the treatment of malignant cells expressing EGFRvIII. Exemplary malignant cells include astrocytomas, glioblastomas, melanoma and the like.

As used herein, "mammalian cells" includes reference to cells derived from mammals including humans, rats, mice, guinea pigs, chimpanzees, or macaques. The cells may be cultured in vivo or in vitro.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

Example 1

We constructed the molecule MR1-1×aCD3, which consists of MR1-1, the murine anti-human EGFRvIII single-chain Fv, and aCD3, the murine anti-human CD3 single-chain Fv. MR1-1×aCD3 was expressed in and purified from bacteria BL21 (DE3), and the activity of this double function molecule was confirmed by FACS showing its specific binding to EGFRvIII-expressing cell lines, as well as human T cells. The cytotoxicity of MR1-1×aCD3 on EGFRvIII-expressing GBM D54MG.EGFRvIII cell lines was measured in vitro by standard chromium release assay. The efficacy of MR1-1×aCD3 was evaluated in NOD/SCID gamma mice where human EGFRvIII-expressing cell lines were implanted. Our results showed that the MR1-1×aCD3 construct is highly cytotoxic and antigen-specific, with an 8-fold increase in specific lysis for D54MG.EGFRvIII over the wild-type control. In a subcutaneous model, tumor growth was inhibited at a dose dependent manner. While total inhibition was achieved at the 100 mcg/mouse/day, low dose might work effectively upon optimization. In summary, our experiments showed that a human EGFRvIII-specific T-cell engaging molecules, MR1-1×aCD3, is effective on EGFRvIII-expressing tumor.

Figure 1:
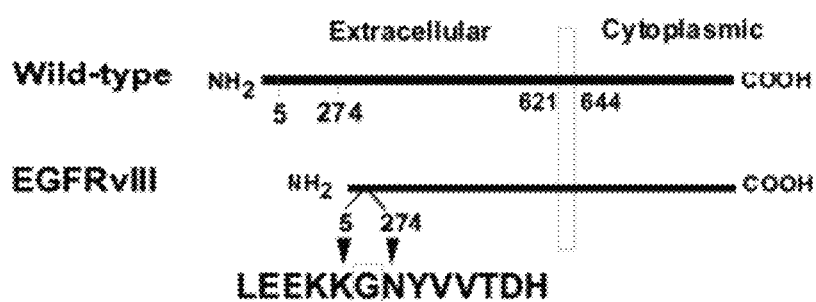
FIG. 1 is a schematic showing the wild-type EGFR and mutant EGFRvIII. PEPvIII: LEEKKGNYVVTDH (SEQ ID NO: 1)
Figure 2:
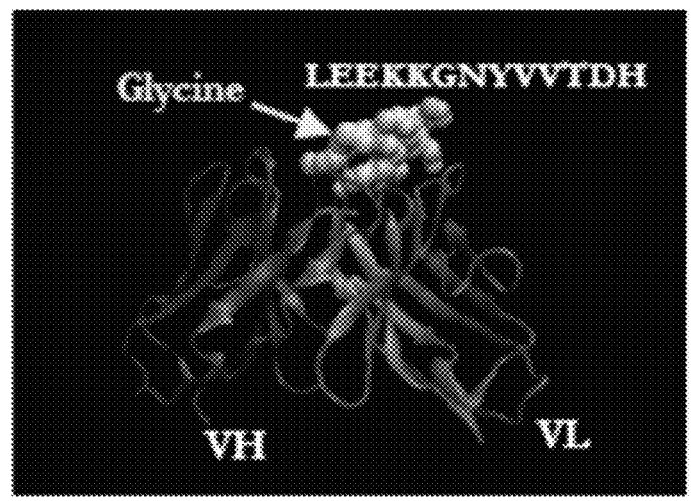
FIG. 2 shows a model of an EGFR specific Fv-PEPvIII (SEQ ID NO: 1) complex.

A murine MAb scFv MR1-1 (FIG. 2), specific for EGFRvIII, has been demonstrated to be a suitable vehicle for GBM treatment in the format of recombinant immunotoxins, which is now in a clinical trial at our institution (BB-IND-12, 589). However, the innate properties of murine-derived antibodies might induce neutralizing antibodies that limit their wider application. Therefore, fully human MAbs are more desirable for the construction of recombinant bispecific T cell engaging molecules for clinical trials.

To obtain high-affinity human anti-EGFRvIII MAbs and scFvs we will (1) fuse EGFRvIII-specific B-cells to the HMMA2.5 non-secreting myeloma partner using an electrofusion technique or (2) clone the variable heavy and light chains from DNA libraries prepared from the antibody-secreting B-cell clones derived directly from GBM patients who have been vaccinated with an EGFRvIII-specific epitope.

Figure 3A:
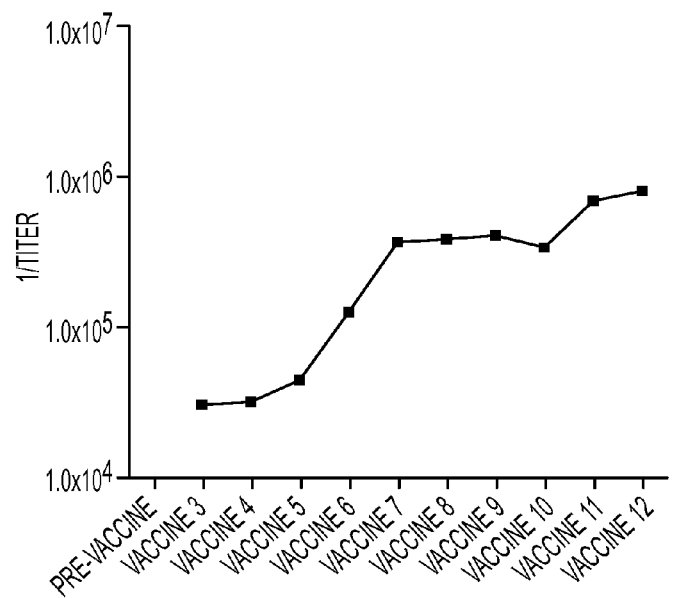
FIG. 3A-3B shows antibody production from GBM patients receiving EGFRvIII-specific vaccination.
Figure 3B:
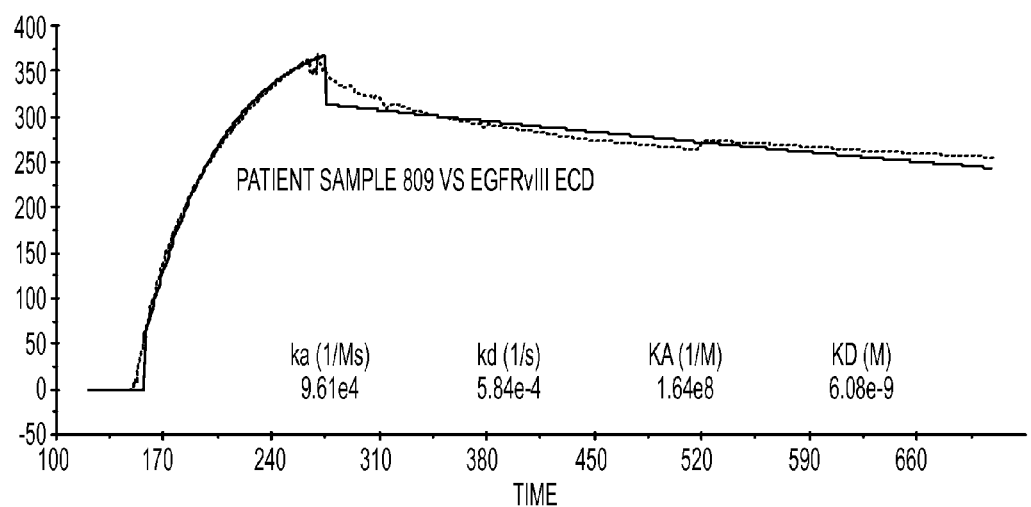

In the context of an ongoing clinical trial in these patients, we have shown that vaccination with an EGFRvIII-specific peptide (PEPvIII: LEEKKGNYVVTDH; SEQ ID NO: 1) induced high-titer antibodies specific to EGFRvIII in 32 of 43 patients, with some patients developing titers >1:2,000,000 (FIG. 3A, Left). Production of high-affinity EGFRvIII-specific antibodies with an average of 6 nM (KD) was confirmed by analyzing EGFRvIII ECD using BIAcore SPR analysis (FIG. 3B, Right).

Figure 4A:
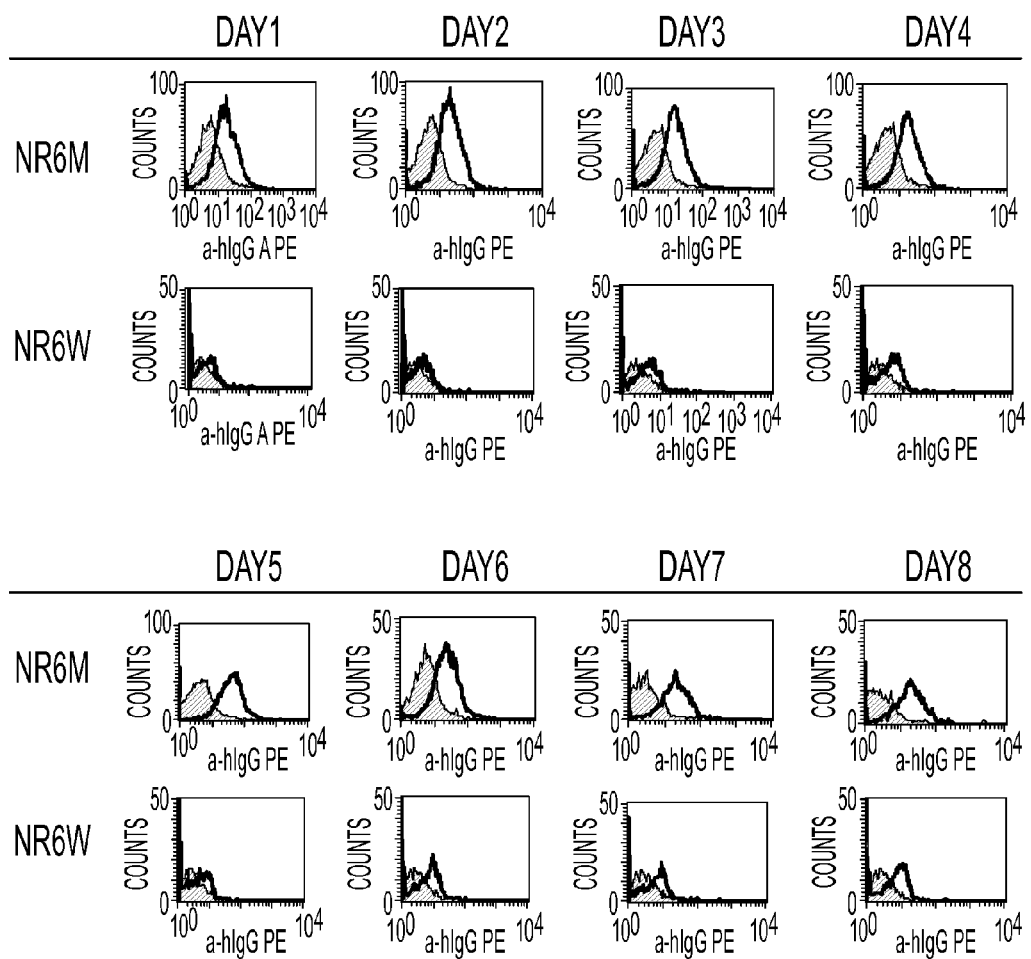
FIG. 4A-4C shows binding of EGFRvIII-specific antibodies from immortalized human B-cells derived from patients with GBM immunized with a peptide containing an EGFRvIII-specific epitope (PEPvIII).
Figure 4C:
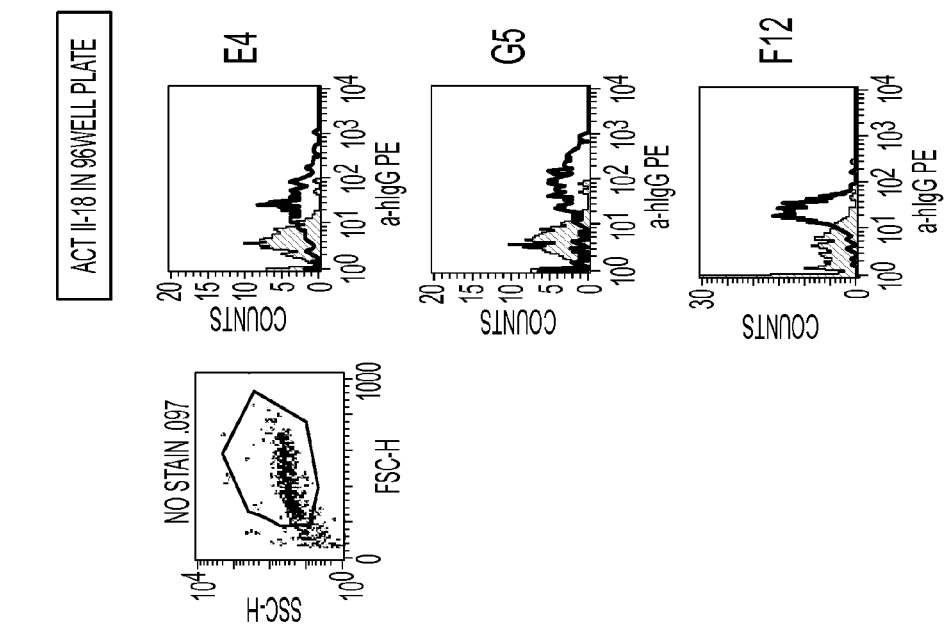
Figure 4B:
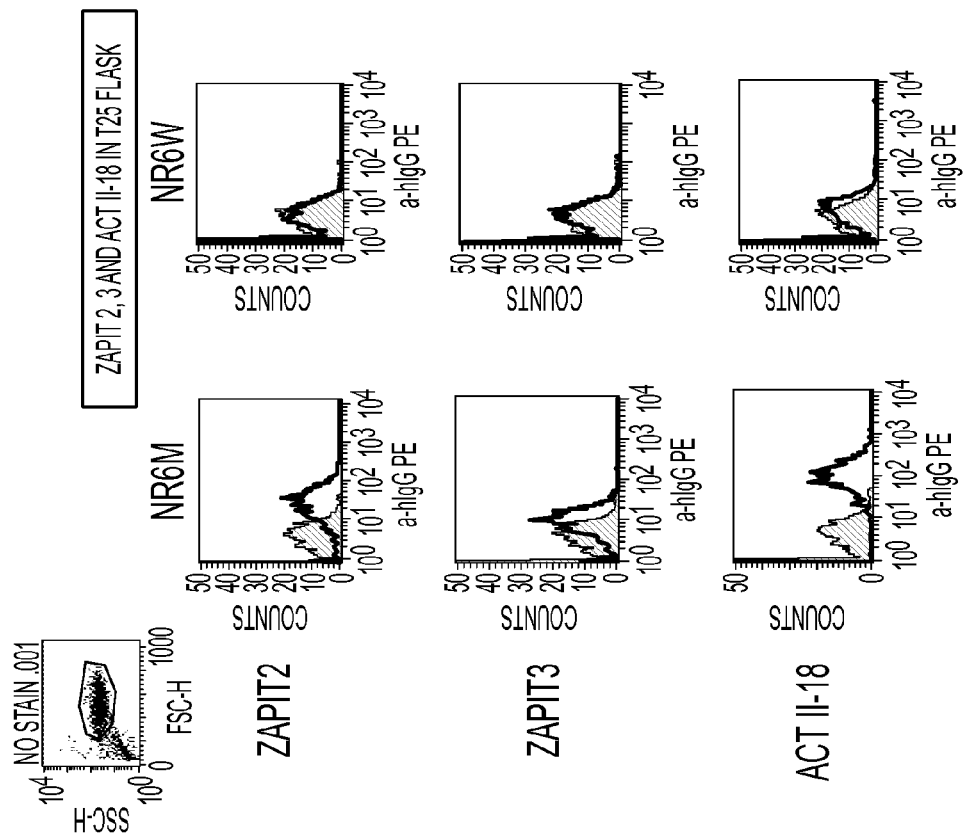

It has often been challenging to clone MAbs directly from human B cells in an efficient way. In our preliminary results, the supernatant derived from human B-cells of a vaccinated GBM patient (ACT II-18 in FIG. 4) after stimulation with PEPvIII demonstrated positive reactivity on EGFRvIII transfected cells (NR6M) and wild-type EGFRwt transfectants (NR6W) at later days (FIG. 4A, Left). With samples from our patients, we were able to transform B-cells with Epstein-Barr virus (EBV), and we demonstrated that these cells maintain their ability to secrete high-titer, EGFRvIII-specific antibodies after peptide stimulation for prolonged periods of at least 2 weeks (FIG. 4B, Middle). In our pilot studies, three out of four patient samples have been successfully transformed and demonstrated high-titer and high-affinity antibody production (FIG. 4C, Right).

Example 2

Figure 5:
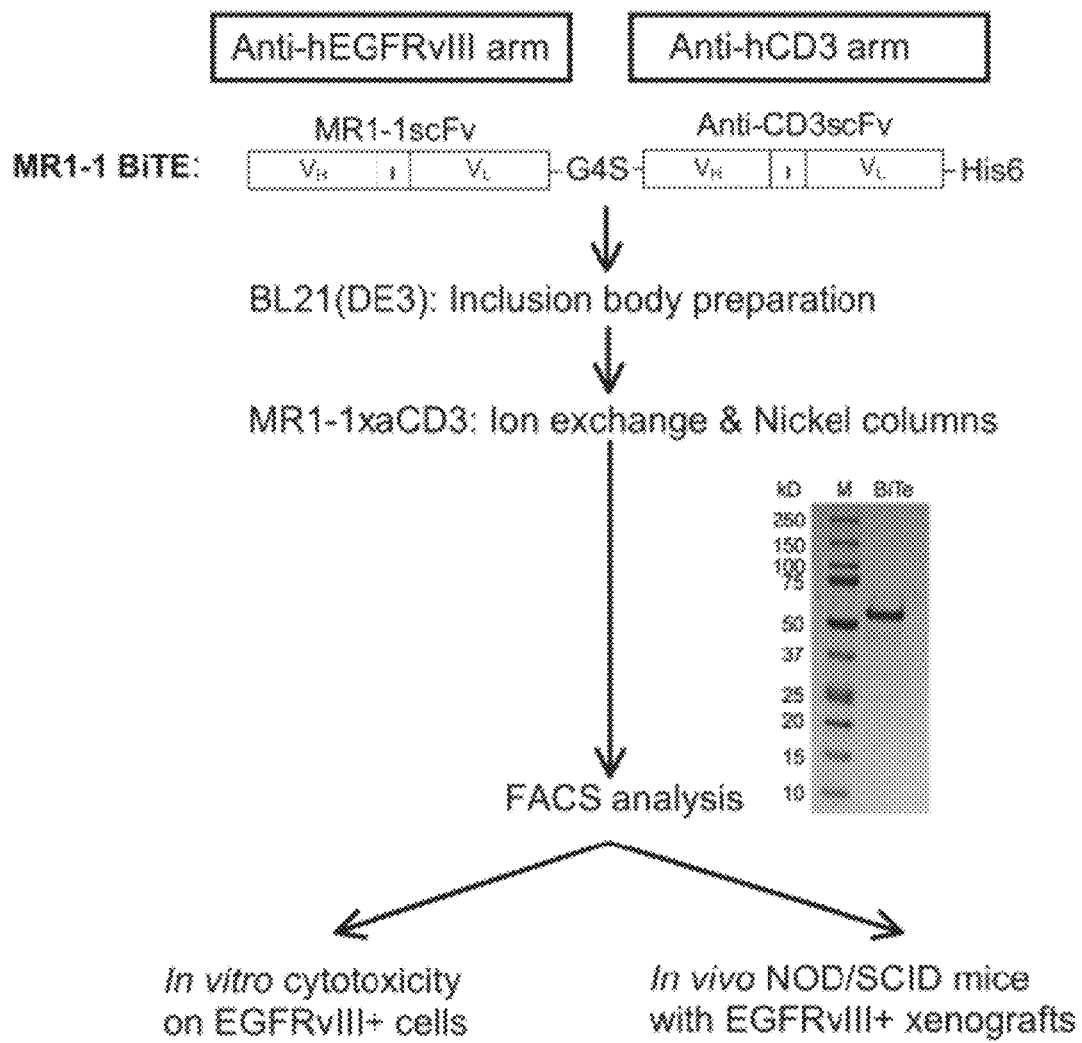
FIG. 5 is a flow diagram showing the generation of recombinant protein MR1-1 scFv-antiCD3scFv-His6 (MR1-1 bispecific T cell engaging molecule). G4S=Gly4Ser; MR1-1×CD3 Bite show in in SDS-PAGE.

To construct a recombinant bispecific T cell engaging molecule based on these human EGFRvIII-specific scFvs, we will subclone the human anti-EGFRvIII scFvs into an existing cassette, which we previously used to create an MR1-1× CD3 molecule (FIG. 5), by substituting the MR1-1scFv portion. Mouse anti-human CD3 scFv was cloned from a hybridoma line OKT3 (ATCC, CRL 8001). MR1-1 bispecific T cell engaging protein after purification was shown in SDS-PAGE gel, with a molecular weight of 55 kDa (FIG. 5; inset). The MR1-1 bispecific T cell engaging molecule binds to EGFRvIII specifically and engages T-cells concomitantly through binding to CD3 (FIG. 6). EGFRvIII binding capacity and specificity was confirmed by using NR6M (EGFRvIII) and NR6W (EGFRwt) cell lines and a GBM cell line transfected with EGFRvIII (U87MG.ΔEGFR) (FIG. 6). Similarly, binding to CD3 was confirmed by staining human peripheral blood mononuclear cells (PBMCs) and Jurkat cells, showing the co-binding of either anti-CD4 or anti-CD8 with bispecific T cell engaging molecules on the same T-cell subpopulation from human PBMC or Jurkat cells (FIG. 7). Although using human scFvs to generate bispecific T cell engaging molecules may reduce the generation of neutralizing antibodies and permit repeated administrations, the existing MR1-1 bispecific T cell engaging molecule may also be used.

Example 3

In order to minimize potential allogeneic responses against the tumor cells, we used our bank of existing matched human peripheral blood lymphocytes (PBLs) and GBM cell lines in these assays. Cytotoxicity of the MR1-1 bispecific T cell engaging molecule was measured by a standard chromium-release assay using unstimulated PBLs as effector cells and human GBM cell line U87MG, which expresses wild-type EGFR, and the transfected U87MG-EGFRvIII cell line as target cells. Results show that the MR1-1 construct is highly cytotoxic and antigen-specific, with a nearly 25-fold increase in specific lysis (%) for U87MGEGFRvIII over the wild-type control, U87MG (FIG. 8A, left). These results echo, if not exceed, the findings that were initially reported in vitro for bscCD19×CD34, a bispecific construct that has since been tested in human trials and found to induce potent tumor regression in patients with non-Hodgkin's lymphoma. The specific lysis by MR1-1 bispecific T cell engaging molecule was at 30% of U87 MG-EGFRvIII compared to ~1%-2% of control cells at 18 h (FIG. 8B, right), showing MR1-1 bispecific T cell engaging molecule mediated dose dependent specific lysis in vitro.

Example 4

The efficacy of MR1-1 bispecific T cell engaging molecule was evaluated in NSG mice. We have determined the MR1-1 bispecific T cell engaging molecule efficacy against U87MGEGFRvIII in NSG mice s.c. Briefly, U87 MG-EGFRIII cells (70%-80% confluence) were harvested with 0.25% Trypsin-EDTA. Cells were washed 2× with sterile PBS. PBLs were harvested as the non-adherent portion from healthy donor PBMC leukaphereses after a 1 h incubation in AIM-V 2% HABS. Three ×105 U87MG-EGFRvIII cells were mixed with 3×105 human PBLs (E:T of 1:1) and injected s.c. into the right flanks of 8 male NSG mice per group. Treatment by tail vein injections with 1 µg, 10 µg, 100 µg, and vehicle control was started 1 h after implantation of tumor cells. Treatment was repeated for four consecutive days. The results showed that the inhibition of subcutaneous U87MG-EGFRvIII tumor growth in NSG mice by MR1-1× CD3 was dose-dependent after 28 days of observation (FIG. 9). Untreated tumor continued to grow steadily. There were two palpable tumors out of 8 in the 1-µg group. There was one palpable tumor in the 10-µg treated group. There were no tumors in the 100-µg treated group. The efficacy of MR1-1 bispecific T cell engaging molecule on the treatment of U87MG-EGFRvIII was very significant and encouraging in terms of the potency and dose dependency.

Example 5

EBV-transformed B cells provide only a transient reservoir of multi-clonal anti-EGFRvIII antibodies due to the high instability of viral incorporation into the human genome. To make stable lines that secrete antibody and to clone EGFRvIII-specific scFvs from these samples, we will use human hybridoma technology and electrofusion as previously described13. Briefly, EBV-transformed PBMCs will be fused with hetermyeloma cell line HMMA2.5 by using a CytoPulse Hybrimune Electrofusion System (Cytopulse). Single cell clones will be screened by HAT (hypoxanthine, aminopterin, and thymidine) selection and confirmed by ELISA of supernatant against recombinant EGFRvIII ECD, or by flow cytometry against EGFRvIII expression cells lines and a cocktail of B-cell markers. Alternatively, we will construct a phage scFv display library expressing human immunoglobulin genes that can be screened on EGFRvIII ECD, and affinity-maturation will be done when needed, as previously described. Another approach will be to bypass the screening step by using high-throughput DNA sequencing and bioinformatic analysis to mine antibody variable region (V)-gene repertoires from plasma cells as described19. VH and VL CDRs of the selected EGFRvIII-specific MAb-expressing hybridomas will be amplified by using isotype-specific primers, and scFv will be constructed in which the scFv protein has been tagged at the carboxy terminus with the hexahistidine sequences for purification and detection. Expression, production, and characterization of scFv will be carried out as described by using a metal affinity column. Binding of scFv will be confirmed by flow cytometry on cells expressing EGFRvIII. At least one fully human anti-EGFRvIII MAb will be isolated and its scFv is expected to have an affinity higher than MR1-1 (1.5 nM).

Example 6

To make the whole anti-EGFRvIII bispecific T cell engaging molecule human, we will generate a human scFv mimotope of murine MAb OKT3 that reacts with CD3 antigen via screening from a human scFv phage display library. The human scFv phagemid library21, obtained from Los Alamos National Laboratory, has very high size ($7.1 \times 10^{13}$ pfu/mL) and diversity ($3 \times 10^{11}$). During selection, the biotinylated target antigen, CD3 (Sino Biological Inc.), is incubated with the scFv library, and complexes formed are captured upon magnetic streptavidin-coated beads. The bead+Ag/scFv complex is washed to remove nonspecific or low-affinity binding phage. The bead+Ag/scFv complex is treated with acid (0.1M HCl) to recover all scFvs that bind to the target antigen. To recover mimics of the mouse antibodies, the bead+Ag/scFv complex will be incubated with the corresponding mouse OKT3 IgG for competition/elution of the binding scFv antibodies. To generate those scFv antibodies with the highest affinity, the selection pressure will be increased through each round for 3 rounds. Once scFvs have been recovered that bind CD3, competition ELISA will be carried out to determine whether they are true mimics of the mouse OKT3, and affinity-maturation will be done if needed. We will then determine the T-cell activation function of 7 the human version OKT3 of anti-CD3 scFv by carrying out (1) T-lymphocyte proliferation assays, (2) cytokine release assays, and (3) detection of the expression of early T-cell activation marker by FACS as described22.

Example 7

We will construct a human anti-EGFRvIII scFv and a human anti-CD3 scFv by linking VH and VL fragments with a (Gly4Ser)3 peptide linker. A hexahistidine tag was introduced at the C-terminus of human anti-CD3 scFv to assist the detection and purification. Expression and purification of the new fully human anti-EGFRvIII bispecific T cell engaging molecule will follow the same protocol as described above for MR1-1 bispecific T cell engaging molecule according to our previous protocol.

Example 8

Building upon these promising preliminary data from our MR1-1 bispecific T cell engaging molecule studies, we will assess the cytotoxic activity of new fully human EGFRvIII-targeted bispecific T cell engaging molecules by following the same protocol as described above. Negative control experiments will be carried out with medium instead of bispecific T cell engaging molecule or effector cells. Specific lysis will then be calculated as [(cpm, experimental release)−(cpm, spontaneous release)]/[(cpm, maximal release)−(cpm, spontaneous release)].

Example 9

The efficacy of novel fully human EGFRvIII bispecific T cell engaging molecules will be evaluated in NSG mice as described previously, as well as in the preliminary studies. Our program has at its disposal a number of EGFRvIII-expressing human GBM xenografts and cell lines with matched autologous lymphocytes cryogenically preserved. Briefly, prior to bispecific T cell engaging molecule administration, tumor cells and lymphocytes will be mixed at a ratio of 1:1 and implanted in the caudate nucleus of the NSG mice using a Kopf stereotactic frame as we previously described24. The NSG mouse model will provide "proof-of-concept" efficacy studies against a GBM expressing EGFRvIII in the CNS. Prior to beginning efficacy experiments, however, a maximum tolerated dose (MTD) of each candidate bispecific T cell engaging molecule will be established in these mice. Individual cohorts of 40 animals each will be administered a candidate molecule, with doses between groups increased by one half log 10 from 0.001 to 1 µg until an MTD is established. On the basis of prior work, mice will be treated intravenously (i.v.) with daily bispecific T cell engaging molecule doses for 5 days. Therapy at the MTD will start after approximately one-third of the median survival time has elapsed according to our prior experience with these tumors. Treatment will consist of the i.v. administration of the bispecific T cell engaging molecule construct at predetermined doses.

REFERENCES

The disclosure of each reference cited is expressly incorporated herein.

1. Stupp R, Mason W P, van den Bent M J, et al: Radiotherapy plus Concomitant and Adjuvant Temozolomide for Glioblastoma. New England Journal of Medicine 352:987-996, 2005
2. Phan G Q, Yang J C, Sherry R M, et al: Cancer regression and autoimmunity induced by cytotoxic T lymphocyte-associated antigen 4 blockade in patients with metastatic melanoma. Proceedings of the National Academy of Sciences of the United States of America 100:8372-7, 2003
3. Suntharalingam G, Perry M R, Ward S, et al: Cytokine storm in a phase 1 trial of the anti-CD28 monoclonal antibody TGN1412. New England Journal of Medicine 355: 1018-28, 2006
4. Bargou R, Leo E, Zugmaier G, et al: Tumor regression in cancer patients by very low doses of a T cell-engaging antibody. Science 321:974-7, 2008
5. Wikstrand C J, Hale L P, Batra S K, et al: Monoclonal antibodies against EGFRvIII are tumor specific and react with breast and lung carcinomas and malignant gliomas. Cancer Research 55:3140-8, 1995
6. Baeuerle P A, Reinhardt C: Bispecific T-cell engaging antibodies for cancer therapy. Cancer Research 69:4941-4, 2009
7. Bigner S H, Humphrey P A, Wong A J, et al: Characterization of the epidermal growth factor receptor in human glioma cell lines and xenografts. Cancer Research 50:8017-8022, 1990
8. Batra S K, Castelino-Prabhu S, Wikstrand C J, et al: Epidermal growth factor ligand-independent, unregulated, cell-transforming potential of a naturally occurring human mutant EGFRvIII gene. Cell Growth & Differentiation 6:1251-1259, 1995
9. Boockvar J A, Kapitonov D, Kapoor G, et al: Constitutive EGFR signaling confers a motile phenotype to neural stem cells. Molecular & Cellular Neurosciences 24:1116-30, 2003
10. Lammering G, Hewit T H, Holmes M, et al: Inhibition of the type III epidermal growth factor receptor variant mutant receptor by dominant-negative EGFR-CD533 enhances malignant glioma cell radiosensitivity. Clinical Cancer Research 10:6732-43, 2004
11. Montgomery R B, Guzman J, O'Rourke D M, et al: Expression of oncogenic epidermal growth factor receptor family kinases induces paclitaxel resistance and alters beta-tubulin isotype expression. Journal of Biological Chemistry 275:17358-63, 2000
12. Archer G E, Sampson J H, Lorimer I A, et al: Regional treatment of epidermal growth factor receptor vIII-expressing neoplastic meningitis with a single-chain immunotoxin, MR-1. Clinical Cancer Research 5:2646-52, 1999
13. Yu X, Tsibane T, McGraw P A, et al: Neutralizing antibodies derived from the B cells of 1918 influenza pandemic survivors. Nature 455:532-6, 200814.
14. Smith, K., arman, L., Wrammert, J., Zheng, N. Y., Capra, J. D., Ahmed, R., and Wilson, P. C. 2009. Rapid generation of fully human monoclonal antibodies specific to a vaccinating antigen. Nature Protocols 4(3): 372-384.
15. Heimberger A, Sun W, Hussain S, et al: Immunological responses in a patient with glioblastoma multiforme treated with sequential courses of temozolomide and immunotherapy. Neuro-Oncology 10:98-103, 2008
16. Wrammert J, Smith K, Miller J, et al: Rapid cloning of high-affinity human monoclonal antibodies against influenza virus. Nature 453:667-71, 2008
17. Wu X, Yang Z Y, Li Y, et al: Rational design of envelope identifies broadly neutralizing human monoclonal antibodies to HIV-1. Science 329:856-61, 2010
18. Beers, R., Chowdhury, P., Bigner, D. and Pastan, I. 2000. Immunotoxins with increased activity against epidermal growth factor receptor vIII-expressing cells produced by antibody phage display. Clinical Cancer Research 6:2835-2843.
19. Reddy S T, Ge X, Miklos A E, et al: Monoclonal antibodies isolated without screening by analyzing the variable-gene repertoire of plasma cells. Nature Biotechnology 28:965-9, 2010
20. Kuan C T, Wikstrand C J, Archer G, et al: Increased binding affinity enhances targeting of glioma xenografts by EGFRvIII-specific scFv. International Journal of Cancer 88:962-9, 2000
21. Sblattero D, Bradbury A. Exploiting recombination in single bacteria to make large phage antibody libraries. Nature Biotechnology 18(1):75-80, 2000.
22. Li B, Wang H, Dai J, et al: Construction and characterization of a humanized anti-human CD3 monoclonal antibody 12F6 with effective immunoregulation functions. Immunology 116:487-98, 2005
23. Kuan C T, Reist C J, Foulon C F, et al: 125I-labeled anti-epidermal growth factor receptor-vIII single-chain Fv exhibits specific and high-level targeting of glioma xenografts. Clinical Cancer Research 5:1539-49, 1999
24. Heimberger A B, Learn C A, Archer G E, et al: Brain tumors in mice are susceptible to blockade of epidermal growth factor receptor (EGFR) with the oral, specific, EGFR-tyrosine kinase inhibitor ZD1839 (iressa). Clinical Cancer Research 8:3496-502, 2002

We claim:

1. A bispecific, T cell engaging polypeptide which binds to EGFRvIII but not to wild-type EGFR, comprising in N-terminal to C-terminal order:
   a first single chain variable region which binds to EGFRvIII;
   a $G_4S$ linker;
   a second single chain variable region which binds to T cell activation ligand CD3;
   wherein the first single chain variable region binds to EGFRvIII but not to wild type EGFR, wherein the first and second single chain variable regions each comprise in N-terminal to C-terminal order a $V_H$ domain, a $(G_4S)_3$ linker, and a $V_L$ domain, and wherein said $V_H$ and $V_L$ domains of the first single chain variable region are antibody MR1-1 $V_H$ and $V_L$ domains, and wherein said $V_H$ and $V_L$ domains of the second single chain variable region are OKT3 $V_H$ and $V_L$ domains.

2. The bispecific, T cell engaging polypeptide of claim 1 wherein each single chain variable region comprises a disulfide bond between the $V_H$ and the $V_L$ domain.

3. The bispecific, T cell engaging polypeptide of claim 1 further comprising a $His_6$ tag.

4. A polynucleotide encoding the bispecific, T cell engaging polypeptide of claim 1.

5. A method of making a bispecific, T cell engaging polypeptide comprising:
   culturing a cell comprising the polynucleotide of claim 4 in a culture medium, expressing said polynucleotide, and collecting the bispecific polypeptide from the cells or culture medium.

6. A method of treating an EGFRvIII-expressing tumor, comprising:
   administering the bispecific, T cell engaging polypeptide of claim 1 to the patient, whereby a cytolytic T cell response to the tumor is induced.

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Leu Glu Glu Lys Lys Gly Asn Tyr Val Val Thr Asp His
1               5                   10
```